(12) United States Patent
Gershonowitz

(10) Patent No.: US 11,717,679 B2
(45) Date of Patent: Aug. 8, 2023

(54) APPARATUS AND METHOD FOR NON-INVASIVE FRACTIONAL TREATMENT OF SKIN TISSUE

(71) Applicant: POLLOGEN LTD., Tel Aviv (IL)

(72) Inventor: Amikam Gershonowitz, Tel Aviv (IL)

(73) Assignee: POLLOGEN LTD., Tel Aviv (IL)

( * ) Notice: Subject to any disclaimer, the term of this patent is extended or adjusted under 35 U.S.C. 154(b) by 0 days.

(21) Appl. No.: 17/324,978

(22) Filed: May 19, 2021

(65) Prior Publication Data

US 2021/0361938 A1   Nov. 25, 2021

Related U.S. Application Data

(60) Provisional application No. 63/027,754, filed on May 20, 2020.

(51) Int. Cl.
| | | |
|---|---|---|
| *A61N 1/36* | (2006.01) | |
| *A61N 1/32* | (2006.01) | |
| *A61N 1/04* | (2006.01) | |

(52) U.S. Cl.
CPC .......... *A61N 1/328* (2013.01); *A61N 1/0408* (2013.01); *A61N 1/0476* (2013.01); *A61N 1/36034* (2017.08)

(58) Field of Classification Search
CPC .. A61N 1/328; A61N 1/36034; A61N 1/0408; A61N 1/0476; A61B 2018/0016; A61B 2018/00452; A61B 2018/0047; A61B 2018/0091; A61B 18/14
See application file for complete search history.

(56) References Cited

U.S. PATENT DOCUMENTS

| | | | | |
|---|---|---|---|---|
| 2005/0049543 | A1* | 3/2005 | Anderson | A61N 1/40 604/20 |
| 2005/0222565 | A1* | 10/2005 | Manstein | A61M 5/158 606/41 |
| 2007/0179482 | A1* | 8/2007 | Anderson | A61B 18/203 606/2 |
| 2012/0158100 | A1 | 6/2012 | Schomacker | |
| 2013/0158634 | A1* | 6/2013 | Ron Edoute | A61N 1/328 607/101 |
| 2014/0088670 | A1* | 3/2014 | Verner Rashkovsky | A61N 1/0476 607/99 |
| 2016/0192854 | A1* | 7/2016 | Liu | A61N 1/0456 600/509 |

(Continued)

OTHER PUBLICATIONS

Search Report and Written Opinion—Corresponding PCT Application No. PCT/IB21/054341, dated Aug. 19, 2021, 13 pages.

*Primary Examiner* — Ankit D Tejani
*Assistant Examiner* — Joshua Brendon Solomon
(74) *Attorney, Agent, or Firm* — Isus Intellectual Property PLLC; Anthony Jason Mirabito

(57) ABSTRACT

The present invention relates to an apparatus for fractional treatment of skin tissue of a patient comprising a handpiece, at least one first electrode and at least one second electrode, arranged on a base plate for applying radio frequency energy, to at least one layer of the skin, wherein the apparatus is adapted to apply electrical energy to the skin tissue with a first pulse and a second pulse following the first pulse, with the first pulse being a low energy level pulse and the second pulse being a high energy level pulse having a higher energy level than the low energy level pulse.

18 Claims, 4 Drawing Sheets

(56) References Cited

U.S. PATENT DOCUMENTS

2019/0059992 A1    2/2019  Ko et al.
2019/0262065 A1    8/2019  Ko et al.
2019/0262066 A1*   8/2019  Ko .......................... A61B 18/14

* cited by examiner

APPARATUS AND METHOD FOR NON-INVASIVE FRACTIONAL TREATMENT OF SKIN TISSUE

The present invention relates to an apparatus and method for fractional treatment of skin tissue.

BACKGROUND OF THE INVENTION

The term fractional treatment in the field of aesthetic medicine is used to describe a form of treatment which creates a discrete array of relatively small treatment spots and leaves a portion of healthy and untouched tissue around these treatment spots. The treatment spots may be created by laser, RF, Ultrasound or other methods. At each spot a micro damage/wound in the tissue is created. The damage/wound at these spots initiates the natural healing response of the tissue. The intact healthy tissue surrounding the treatment spots are vital enough basis to provide what is necessary for healing the micro wounds. The overall effect is skin rejuvenation.

SUMMARY

An object of the current disclosure is to an apparatus and a method according to the independent claims. In particular, an apparatus for fractional treatment of skin tissue of a patient; the apparatus comprising: a handpiece; at least one first electrode and at least one second electrode, the at least one first electrode and the at least one second electrode being arranged on the distal end portion of the handpiece; and an energy source connected to said at least one first electrode and to at least one second electrodes. Wherein the apparatus is configured to apply electrical energy, to at least one layer of the skin, wherein the at least one first electrode and the at least one second electrode (are co-planar and are arranged on a base plate. Also, wherein the apparatus is configured to apply the electrical energy to the skin tissue with at least one initial pulse and a treatment pulse following the at least one initial pulse with the at least one initial pulse and the treatment pulse being at least one of the following:
 (i) a low energy level at least one initial pulse followed by a higher energy treatment pulse;
 (ii) a shorter duration at least one initial pulse followed by a longer duration treatment pulse; or
 (iii) a shorter duration high energy at least one initial pulse followed by a longer duration low energy pulse.

In another objective, there is the apparatus where at least one first electrode and the at least one second electrode are at least one of the following: (i) co-planar with the base plate; (ii) flat with the base plate; or (iii) form a slight elevation above the base plate. The apparatus wherein the at least one second electrode surrounds and concentrically encircled by a section thereof, the at least one first electrode. Also, wherein the at least one second electrode, is one single second electrode, substantially covers the base plate.

The apparatus, wherein the at least one first electrode is a plurality of first electrodes arranged in at least one of the following arrangements: (i) one row; (ii) a plurality of rows; (iii) in particular rows arranged in parallel; or (iv) in particular rows discretely spaced apart from each other. The apparatus further comprising: a vacuum chamber within the handpiece, the vacuum chamber being in fluid communication with at least one through hole or gap provided in the base plate configured to provide a negative pressure force on a surface of the skin tissue towards the at least one first electrode and to draw the skin tissue towards the at least one second electrode. The at least one first electrode and the at least one second electrode is placed in at least one of the following positions: (i) in proximity of the skin tissue; or (ii) in contact with the surface of the skin tissue.

In another objective of the current disclosure, the apparatus, wherein the at least one second electrode is arranged on the base plate and the at least one first electrode comprises a pin, which penetrates the base plate through an aperture in the base plate. The apparatus, wherein the at least one initial pulse is configured to reduce the impedance of the uppermost layer or layers of the skin tissue. The apparatus, wherein the at least one initial pulse is not configured for performing an ablative process, and not sufficient for ablating the uppermost layer of the skin tissue. The apparatus, wherein the treatment pulse is configured to perform thermal damage without ablation within a dermis layer or a hypodermis layer of the skin tissue.

The apparatus is configured to perform a non-invasive treatment of the skin tissue, that thermally treat cells in the dermis layer or the hypodermis layer of the skin, without penetrating or ablating the surface of the skin tissue. The apparatus, wherein the at least one first electrode is of a two-dimensional extension, in particular a circular area with a diameter between 0.1 and 1 mm, preferably about 0.5 mm. The apparatus, wherein the plurality of first electrodes have the same polarity and the at least one second electrode has an opposite polarity. The apparatus, wherein the plurality of rows is arranged on a flat base plate. The apparatus, wherein the plurality of rows is arranged on a roller surface.

In another objective there is a method for fractional treatment of skin tissue of a patient, in particular of cells in the dermis layer or the hypodermis layer, the method comprising:
 touching a surface of the skin tissue, with a handpiece of a treatment apparatus, the handpiece comprising: at least one first electrode, and at least one second electrode;
 supplying the at least one first and the at least one second electrode with radio frequency (RF) energy;
 applying, by the handpiece, the RF energy to the skin tissue,
  wherein an at least one initial pulse of RF energy is followed by a treatment pulse of RF energy and, wherein the at least one initial pulse (21) and the treatment pulse (22) combination comprising at least one of the following:
   (i) at least one low energy total usage pulse followed by at least one high total energy usage pulse;
   (ii) at least one shorter duration pulse followed by at least one longer duration pulse; or
   (iii) a high peak energy pulse followed by a low peak energy pulse.

In yet another objective, there is the method, wherein the initial pulse is configured to reduce the impedance of the uppermost layer or layers of the skin tissue, and the treatment pulse is configured to perform thermal damage within the dermis layer or the hypodermis layer of the skin tissue. The method, wherein the length of the at least one initial pulse is between 1 and 10 ms; and the length of the treatment pulse is between 0.1 and 10 s. The method, wherein the length of the at least one initial pulse is about 5 ms; and the length of the treatment pulse is at least one of the about 1 s.

BRIEF DESCRIPTION OF THE FIGURES

Some embodiments of the claimed apparatus and/or method will be described in the following by way of example only, and with reference to the accompanying figures, in which

DETAILED DESCRIPTION

Various example embodiments will now be described more fully with reference to the accompanying drawings in which some embodiments are illustrated.

Fractional treatment may be referred to generally as ablative or non-ablative, although in some retreatment regimes a combination may be applied. The discrete damaged spots may be skin portions in which the energy source has ablated the tissue, evaporated the tissue or just heated the tissue for a certain amount of time. RF energy may be emitted by a single electrode or an array of electrodes. In a bi-polar form of RF, two adjacent electrodes are paired with opposite polarity to heat the tissue located between and below the pair of electrodes. Usually, the penetration depth of the RF electrical field between two working bipolar electrodes is about half of the distance between the electrodes.

For certain skin rejuvenating treatment regimes, tissue located at the hypodermis, dermis or epidermis layer of the skin is targeted to be treated. The top layer of skin is known as the stratum corneum cells layer and is characterized by the lack of interstitial fluid, and this dry layer of cells creates high electrical impedance barrier for any external electrode configured to deliver energy into the skin. The epidermis is characterized by a low electrical impedance due to the existence of an interstitial fluid. Therefore, the stratum corneum, the outermost layer of the skin, is usually penetrated before treatment Many treatments of fractional RF devices do ablate the stratum corneum in order to establish conductive non-ablative coupling between the working electrodes and the upper layers of the epidermis, located below the stratum corneum. The damage, however, created by these non-ablative technologies to the protecting layer of the stratum corneum, exposes the epidermis and may be a source for contamination and complications.

Figure 1:
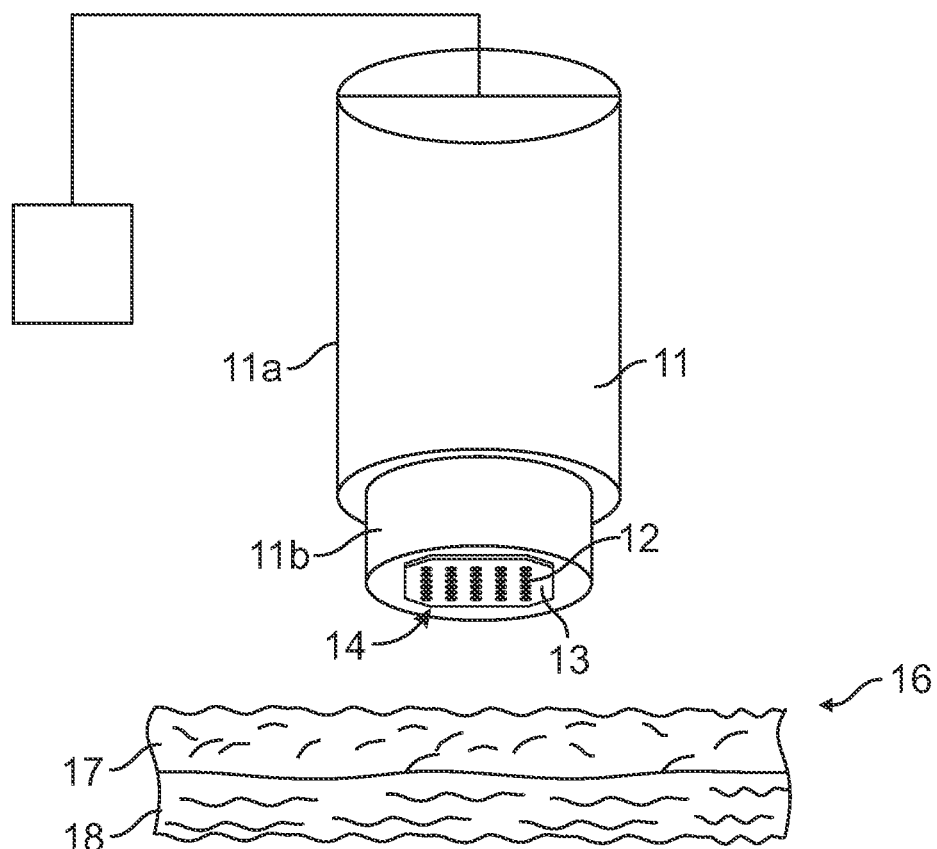
FIG. 1 shows an apparatus for fractional treatment of skin tissue.

FIG. 1 illustrates a system or apparatus, of some embodiments of the current technology, for fractional treatment 10 of skin tissue 16. In some embodiments, the fractional treatment is non-ablative, but nevertheless creates an array of discrete thermal affected zones to establish coagulation zones and initiate rejuvenation effect. In some embodiments, the current disclosed technology is fractional RF treatment protocol which targets dermal layers below the stratum corneum while keeping the stratum corneum intact.

The skin tissue 16 comprises an outer layer, the stratum corneum 17, which has a higher impedance than the epidermis, the dermis or the hypodermis 18 below it. The fractional RF devices are intended to create thermal affected zones in the epidermis and/or dermis and/or hypodermis 18 and therefore, according to the state of the art, break up the stratum corneum 17 by ablation. If this is done without inserting needles, such procedure is considered as a non-invasive.

The apparatus of the current disclosure, in some embodiments, comprises an energy source 15 which emits RF energy, which is transmitted to a distal end of a handpiece comprising a base plate 14, in particular to at least one first electrode 12 or to both, at least one first 12 and at least one second electrode 13 for bipolar systems. In some embodiments, the base plate 14, which comprises the electrodes 12 and 13, is attached, arranged or mounted to a handpiece 11. In some embodiments, the second electrode (13), is one single second electrode, substantially covering the base plate (14) but not the first electrodes. The handpiece 11 may comprise a housing. In some embodiments, the handpiece 11 comprises a main body 11a and a detachable head 11b comprising the base plate 14, electrodes 12 and 13. In some embodiments, the detachable head 11b further comprises a vacuum chamber. In some embodiments, the detachable head of the handpiece is connected to the main body by means of a Snap-on, latch connection, a bayonet fitting or any combination thereof. In some embodiments, base plate 14 is directed against a portion of a patients' skin tissue 16 to be treated. The desired effect of damaging/wounding the skin tissue 16 takes place in the epidermis, dermis or hypodermis layer 18 of the skin 16.

Figure 2:
FIG. 2 shows a pulse sequence.

FIG. 2 illustrates a pulse sequence, which may be used for transmitting the RF electrical energy 20. In some embodiments, the stratum corneum 17 is not ablated in order to effect and damage treatment zones in the dermis or hypodermis. In some embodiments, an initial pulse 21 is followed by a treatment pulse 22. In some embodiments, the initial pulse 21 is a low-level energy usage, which is insufficient to ablate the stratum corneum 17, but will change the stratum corneum's impedance during the time of the pulse and dynamically change the stratum corneum's 17 impedance such that its impedance is reduced, which in consequence allows the treatment pulse 22 to accomplish the desired thermal damage. In this way, an ablation of the stratum corneum can be avoided or minimized. The treatment pulse 22 causes the fractional thermal damage within the epidermis, dermis or hypodermis layers, which is considered to be a driving force for skin rejuvenation.

In some embodiments, during the initial pulse, the skin cells are shocked or otherwise disturbed by very gently disrupting the cells so that extra cellular fluids from the epidermis in layer 18 below rise and wet the normally dry stratum corneum 17, thus reducing its impedance. In consequence, no stratum corneum 17 ablation is necessary.

The apparatus 11 applies electrical energy 20 to the tissue 16 with the initial pulse 21 and a following treatment pulse 22. In some embodiments, the initial pulse 21 is a low energy usage pulse and the treatment pulse 22 is a high energy usage pulse, i.e. has a higher energy totally used than the initial pulse 21. In some embodiments, the initial pulse is shorter duration then the treatment pulse and the treatment pulse are a longer duration then the initial pulse. In some embodiments, the initial pulse is a higher peak energy and the treatment pulse is a lower peak energy. In some embodiments, the initial pulse is of a shorter duration, low energy usage and higher peak energy and the treatment pulse is a high total energy usage, a longer duration, and a lower peak energy level. In some embodiments, there is at least one or more initial pulses and the treatment pulse at least one or more treatment pulses. In some embodiments, there is a series of 3 initial pulses of a shorter duration, low energy usage and higher peak energy and the treatment pulse is a series of at least two treatment pulses of high total energy usage, longer duration, and lower peak energy level. The pulse properties as compared to each other, i.e. the higher peak energy level of the initial pulse compared to the lower peak energy of the treatment pulse.

In some embodiments, the initial pulse 21 is between 1 and 10 ms and the length of the treatment pulse 22 is between 0.1 and 10 s duration. In some embodiment, the initial pulse may be about 5 ms (+/−50%) and treatment pulse may be about 1 s (+/−50%) durations. In some embodiments, the initial pulse 21 is more than one pulse in a series of initial pulses. In some embodiments, the initial pulse is a series of three first pulses.

Figure 3A:
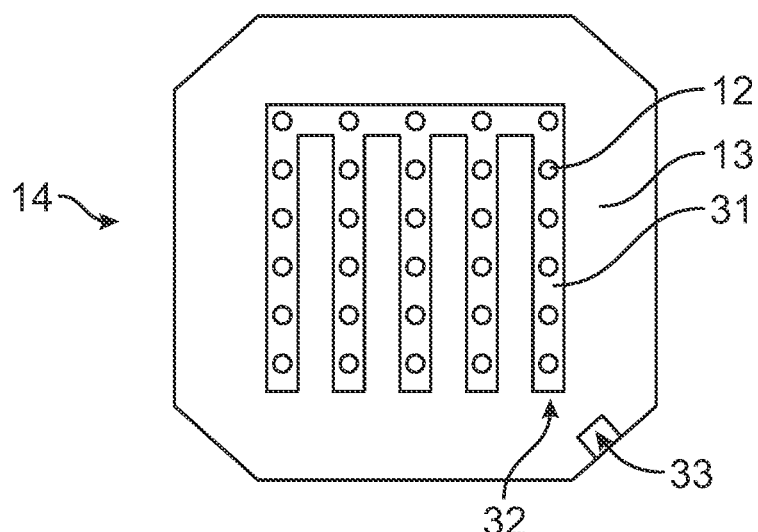
FIG. 3a shows an embodiment of abase plate, in some embodiments of the currently disclosed technology.
Figure 3B:
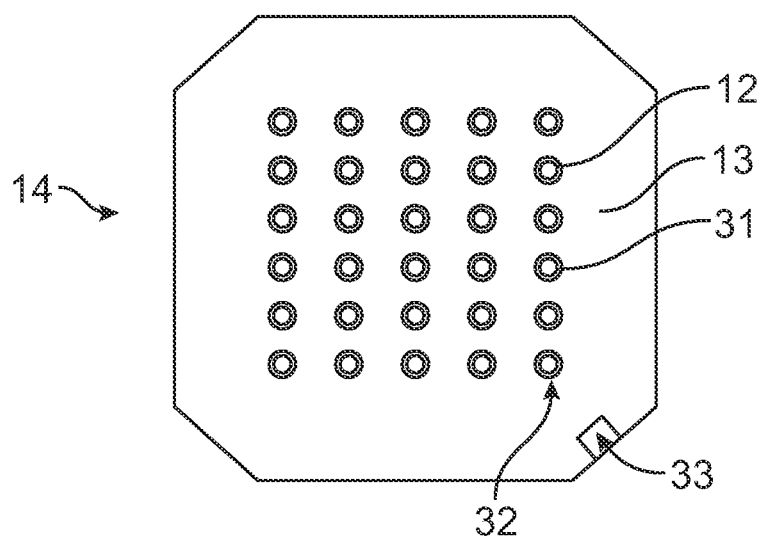
FIG. 3b shows an embodiment of a base plate, in some embodiments of the currently disclosed technology.

FIGS. 3a and 3b illustrate base plates 14, which are attached or mounted onto the distal end of the handpiece 11. In some embodiments, the handpiece comprises a main body 11a and a detachable head 11b further comprising the base plate. In some embodiments, the detachable head of the handpiece is connected to the main body by means of a snap-on, latch connection, a bayonet fitting or any combination thereof. In some embodiments shown in FIGS. 3a and 3b, the base plates have very short or shallow contact surfaces (i.e. first electrodes 12) which are designed so as to not penetrate or pierce the skin 16. However, they achieve an effective treatment in the hypodermis or dermis layers 17 and 18 of the skin.

In some embodiments, electrodes 12 are charged with electrical energy against a second electrode 13 formed by a metallic layer, covering the base plate 14 and surrounding the array of electrodes 12. In some embodiments, all of the first electrodes have the same polarity, while the second electrode 13 has a different polarity. In some embodiments, the metallic layer is a gold layer. In some embodiments, second electrode 13 is an opposite polarity to the first electrode 12. In some embodiments, the base plate is a square with a measurement on each side between about 10 and 18 mm.

In some embodiments, the metallic layer 13 is not a full-surface cover, but rather the metallic layer or the base plate includes a plurality of circular apertures/holes/insulating gaps 31. In some embodiments, the apertures 31 are any shape. In some embodiments, the first electrodes are isolated from the second electrodes. Each of the electrodes 12 may be positioned in the center of one of the circular apertures/holes/insulating gaps 31. Since the diameter of the circular holes 31 is greater than the diameter of the electrodes 12, the circular holes 31 provide an annular gap, and in this way an insulation zone, between electrodes 12 in the hole centre and the surrounding metallic layer 31. In some embodiments, the circular holes have a diameter between about 1 to 2 mm.

In some embodiments, thermal treatment is provided when the first and second electrodes are supplied with radio frequency (RF) energy by means of the power unit 15 forming an electrical energy source. In some embodiments, the first electrodes are connected to a first pole of the RF energy source and the metallic layer forming the second electrode 13 is connected to a second pole of the RF energy source. In some embodiments, the RF energy applied on skin tissue causes the skin temperature to increase, which is not only a function of energy intensity but also a function of the pulse width of the applied RF energy.

In some embodiments, the plurality of first electrodes 12 may be arranged in at least one row 32. In some embodiments, the plurality of first electrodes is arranged in a plurality of rows. In some embodiments, the plurality of rows 32 are arranged in parallel and/or discretely spaced apart from each other.

FIG. 3a, illustrates, in some embodiments, the return plate, i.e. second electrode 13 extends between the pins/first electrodes 12, and in particular the fingers of the second electrode 13 are located between the rows 32 of pins. In some embodiments, the majority (i.e. more than 50, 70, 80 or 90%) of the surface of the base plate 14 is covered by the second electrode 13. In some embodiments, the second electrode 13 has zero height (except for the conductive layer of the electrode) and is flat and co-planar relative to the base plate 14. In some embodiments, the first electrodes 12 are flat and co-planar or are only slightly elevated above the base plate 14. In some embodiments, the elevation of first electrodes 12 are less than 30, 20, 10, 5, and 1% of the distance between two adjacent first electrodes 12.

In some embodiments, and as illustrated in FIG. 3b, the second electrode 13 surrounds, in particular concentrically encircled by a section thereof, at least one first electrode 12. In some embodiments, due to this geometrical layout, the distance between one of the first electrodes 12 and the closest area of the second electrode is always the same and is defined by the size of gaps 31.

As noted above, the penetration depth of the RF electrical field is a function of the size of gap 31. In the example shown in FIG. 3b, all gaps 31 have the same dimensions and therefore the penetration depth of the RF electrical field is the same across and over the whole base plate 14, i.e. for each electrode 12. However, in some embodiments, different electrodes 12 may have different gaps with electrode 13 and therefore different penetration depths may be achieved. For example, a first subgroup of electrodes 12 may have a first gap 31 and a second subgroup of electrodes 12 may have a different gap 31. The first sub-group may be, for example, a first row 32 and the second sub-group may be, for example, a second row 32.

In some embodiments, an orientation marker 33 at a corner or edge of the base plate 14 aids in assuring a correctly-orientated assembly of the base plate 14 onto the handpiece 11.

In some embodiments, the fluence in the device is reduced by increasing the diameter of the electrodes 12. In some embodiments, the diameter of the first electrode 12 is about 0.5 mm in diameter. As the area of the tip is larger, the field lines spread among a larger area and in consequence reduce the fluence.

In some embodiments, the first electrodes 12 have a two-dimensional extension, in particular a circular area with a diameter between 0.1 and 1 mm. In some embodiments, have a two-dimensional extension with a circular area with a diameter of about 0.5 mm.

Figure 3C:
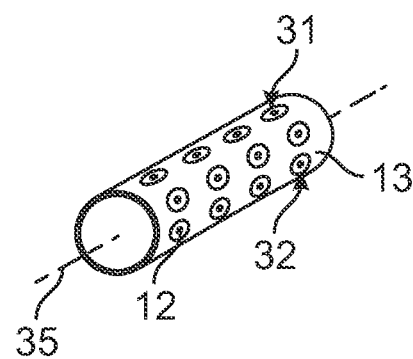
FIG. 3c shows a roller.

FIG. 3c illustrates, in some embodiments of the disclosed technology, a roller 34 with a cylindrical surface instead of a plane flat surface as described for FIG. 3a, 3b. In some embodiments, the roller is configured like base plate 14. In some embodiments, the roller 34 has an axis 35 which may be attached to and supported by a handpiece. The ability to spin around the axis 35 allows a rolling over the skin 16 surface of the patient during treatment.

Figure 4:
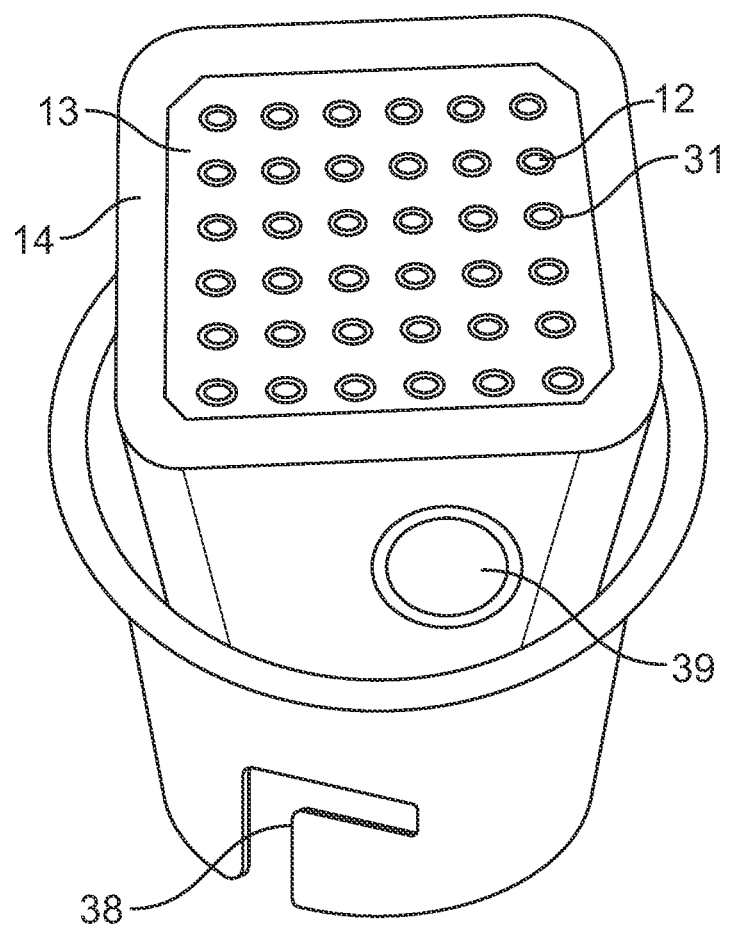
FIG. 4 shows a detachable head part including the base plate.

FIG. 4 shows, in some embodiments, apparatus 10 further comprising a vacuum chamber in fluid communication with a vacuum port 39 for connecting the vacuum chamber to a vacuum source (e.g. a pump located inside or outside of the handpiece 11). In some embodiments, the vacuum chamber is also in fluid communication with through holes 31 provided in the base plate 14 for exerting an attractive force on a surface of the skin tissue to draw it towards the first electrodes 12 and towards the second electrode 13, when the first electrodes and the second electrode are placed in proximity of or is in contact with the surface of the skin tissue. In some embodiments, the electrodes 12, 13, the baseplate 14 and the vacuum chamber 36 are arranged in a detachable head part of the handpiece 11, which may be connected via a bayonet fitting 38. In some embodiments, the vacuum chamber is located within the housing of the handpiece and defined by the base plate at a front side, a rear plate at a rear side and the housing the housing of the head of the handpiece, in radial direction. The rear plate may be in an at least approximately parallel alignment with the base plate. In some embodiments, at least one of the base plate and the rear plate is or comprises a printed circuit board.

Figure 5A:
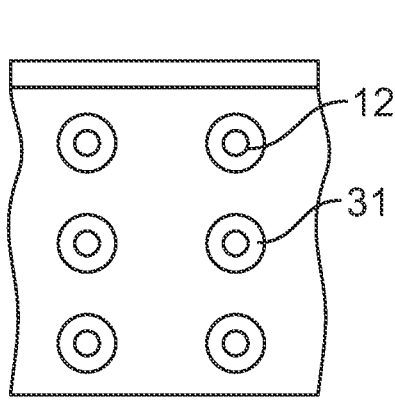
FIG. 5a is a detailed view of the base plate of FIG. 4.
Figure 5B:
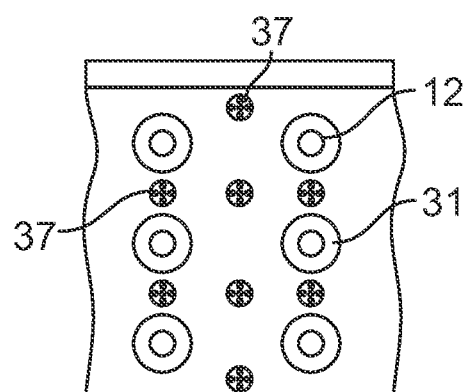
FIG. 5b shows an embodiment of the base plate, in some embodiments of the currently disclosed technology.

FIG. 5a shows a detailed view, of some embodiments, of the base plate of FIG. 4. FIG. 5b shows a view, of some embodiments, of the base plate, which comprises through holes 37 which do not have electrodes and are in fluid communication with the vacuum chamber 36 located behind the base plate 14. In some embodiments, insulating gaps 31 are not designed as through holes in the base plate 14 but only areas of the base plate 14 which are not coated by an electrically conductive layer forming the second electrode 13.

Figure 6:
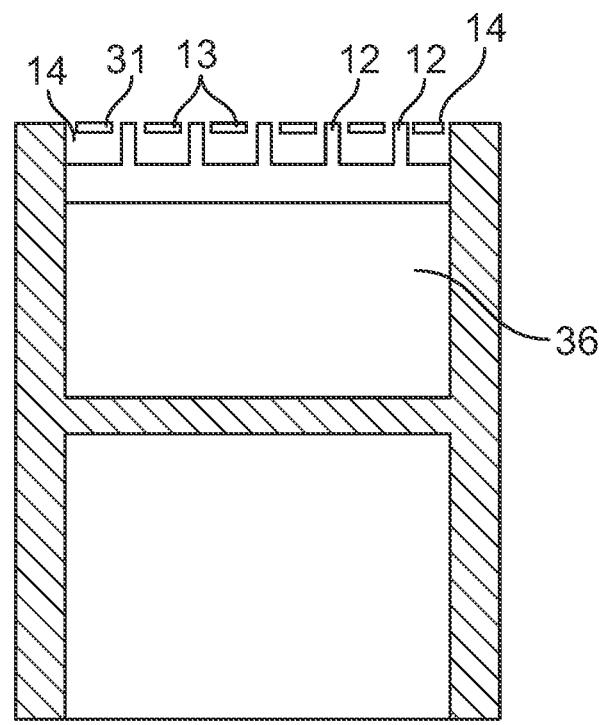
FIG. 6 is a sectional view of FIG. 4.
Figure 7:
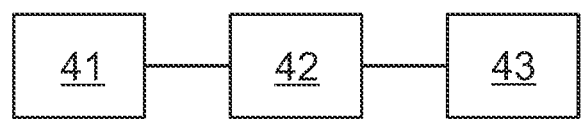
FIG. 7 shows the method steps of the invention.

FIG. 6 shows a cross sectional view of FIG. 4. In some embodiments, the detachable head comprises a vacuum chamber 36 which is in fluid communication with the insulating gaps 31 which are provided as through holes in the base plate 14. In some embodiments, first electrodes 12 are provided by an array of pins 12 arranged on a comb-like structure penetrating the insulating gaps 31. As can be seen in this cross-sectional view, in some embodiments, the second electrode 13 is formed as a coating on the base plate 14. In some embodiments, the first electrodes 12 and the second electrode 13 are arranged so as to be co-planar. In some embodiments, the pins 12 do not protrude from the insulating gaps 31 and from the second electrode 13. In some embodiments, the pins protrude from the insulating gaps 31 less than 30, 20, 10, 5, or 1% of the distance between two neighbouring first electrodes 12.

FIG. 5 illustrates a flow chart including method steps in some examples of the currently disclosed method.

In step 41, of fractional treatment 40 comprises touching a surface of the skin 16 with the distal end of the handpiece 11 and positioning the electrodes 12, 13 against the skin surface.

In step 42, of some embodiments of the current disclosure, an initial at least one pulse 21 of RF electrical energy 20 is applied. In some embodiments, the at least one initial pulse is chosen from one of the following; low total energy used than a treatment pulse, shorter duration than a treatment pulse, higher peak power than a treatment pulse, or any combination thereof.

In step 43, at least one treatment pulse 22 of RF electrical energy 20 is applied causing a thermal damage in the dermis or hypodermis. In some embodiments, the at least one treatment pulse is chosen from one of the following; high total energy used than a initial pulse, shorter duration than an initial pulse, lower peak power than an initial pulse, or any combination thereof.

In some embodiments, apparatus and method disclosed above is used for treating dry eye syndrome of a patient. One reason for dry eyes is blepharitis, a chronic inflammation of the eyelid margin. It has been shown that heating up the area of a Meibomian Gland has a long-lasting effect and bacteria and skin mites are successfully eliminated. A RF energy source may be used to generate heat, so as to heat up the area of a Meibomian Gland. In some embodiments, when used for treating dry eye syndrome, the apparatus comprises a head part (not shown) with a flexible distal end portion for adapting to the curvature of the eye ball. In some embodiments, a flexible printed circuit board configured to bend on contact with the eyelid and conform to the shape of the eyelid is utilized.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "a", "an" and "the" mean "one or more", unless expressly specified otherwise.

A description of an embodiment with several components in communication with each other does not imply that all such components are required. On the contrary a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated operations of FIG. 5 show certain events occurring in a certain order. In alternative embodiments, certain operations may be performed in a different order, modified, or removed. Moreover, steps may be added to the above-described logic and still conform to the described embodiments. Further, operations described herein may occur sequentially or certain operations may be processed in parallel. Yet further, operations may be performed by a single processing unit or by distributed processing units.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of the invention is intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. An apparatus for fractional treatment of skin tissue of a patient;
   the apparatus comprising:
      a handpiece;
      at least one first electrode and at least one second electrode, the at least one first electrode and the at least one second electrode being arranged on a base plate at the distal end portion of the handpiece; and an energy source connected to said at least one first electrode and to said at least one second electrode, wherein the apparatus is configured to apply electrical energy, through said at least one first electrode and said at least one second electrode, to one site of the skin tissue, and wherein the apparatus is configured to apply the electrical energy to treat the one site of the skin tissue with at least one first pulse and at least one second pulse following the at least one first pulse with the at least one first pulse and the subsequent at least one second pulse combination comprising the following:

(i) a low energy total usage, for the at least one first pulse, followed by a high total energy usage, for the at least one second pulse;

and (ii) a high peak energy, for the at least one first pulse, followed by a low peak energy, for the at least one second pulse.

2. The apparatus according to claim 1, wherein the at least one first electrode and the at least one second electrode are at least one of the following;
   (i) co-planar,
   (ii) flat with the base plate, or
   (iii) form a slight elevation above the base plate.

3. The apparatus according to claim 1, wherein the at least one second electrode surrounds and concentrically encircled by a section thereof, the at least one first electrode.

4. The apparatus according to claim 1, wherein the at least one second electrode, is one single second electrode, substantially covering the base plate.

5. The apparatus according to claim 1, wherein the at least one first electrode is a plurality of first electrodes arranged in at least one of the following arrangements:
   (i) one row;
   (ii) a plurality of rows;
   (iii) in particular rows arranged in parallel; or
   (iv) in particular rows discretely spaced apart from each other.

6. The apparatus according to claim 1, the apparatus further comprising:
   a vacuum chamber within the handpiece, the vacuum chamber being in fluid communication with at least one through hole or gap, provided in the base plate, configured to provide a negative pressure force on a surface of the skin tissue towards the at least one first electrode and to draw the skin tissue towards the at least one second electrode, when the at least one first electrode or the at least one second electrode is placed in at least one of the following positions:
   (i) in proximity of the skin tissue; or
   (ii) in contact with the surface of the skin tissue.

7. The apparatus according to claim 1, wherein the at least one second electrode is arranged on the base plate and the at least one first electrode comprises a pin, which penetrates the base plate through an aperture in the base plate.

8. The apparatus according to claim 1, wherein the at least one first pulse is configured to reduce the impedance of the uppermost layer or layers of the skin tissue.

9. The apparatus according to claim 1, wherein the at least one first pulse is configured for performing a non-ablative process, and is not sufficient for ablating the uppermost layer of the skin tissue.

10. The apparatus according to claim 1, wherein the second pulse is configured to perform thermal damage without ablation within a dermis layer or a hypodermis layer of the skin tissue.

11. The apparatus according to claim 1, wherein the apparatus is configured to perform a non-invasive treatment of the skin tissue, that thermally treats cells in the dermis layer or the hypodermis layer of the skin, without penetrating or ablating the surface of the skin tissue.

12. The apparatus according to claim 1, wherein the at least one first electrode is of a two-dimensional extension, in particular a circular area with a diameter between 0.1 and 1 mm.

13. The apparatus according to claim 5, wherein the plurality of first electrodes have the same polarity and the at least one second electrode has an opposite polarity.

14. The apparatus according to claim 5, wherein the plurality of rows is arranged on a flat base plate.

15. The apparatus according to claim 5, wherein the plurality of rows is arranged on a roller surface.

16. A method for fractional treatment of skin tissue of a patient, in particular of cells in the dermis layer or the hypodermis layer, the method comprising:
   touching a surface of the skin tissue, with a handpiece of a treatment apparatus, the handpiece comprising: at least one first electrode, and at least one second electrode;
   supplying the at least one first and the at least one second electrode with radio frequency (RF) energy;
   applying, by the handpiece, the RF energy to the skin tissue,
   wherein at least one first pulse of RF energy is followed by at least one second pulse of RF energy and,
   wherein the at least one first pulse and the at least one second pulse combination comprising the following:
   (i) a low energy total usage, for the at least one first pulse, followed by a high total energy usage, for the at least one second pulse;
   and
   (ii) a high peak energy, for the at least one first pulse, followed by a low peak energy, for the at least one second pulse.

17. The method according to claim 16, wherein the at least one first pulse is configured to reduce the impedance of the uppermost layer or layers of the skin tissue, and the at least one second pulse is configured to perform thermal damage within the dermis layer or the hypodermis layer of the skin tissue.

18. The method according to claim 16, wherein the length of the at least one first pulse is between 1 and 10 ms; and the length of the at least one second pulse is between 0.1 and 10 s.

* * * * *